US00RE36419E

United States Patent [19]

Cavanaugh, Jr.

[11] E Patent Number: Re. 36,419

[45] Reissued Date of Patent: Nov. 30, 1999

[54] USE OF KETOROLAC FOR TREATMENT OF SQUAMOUS CELL CARCINOMAS OF THE ORAL CAVITY OR OROPHARYNX

[75] Inventor: Paul Francis Cavanaugh, Jr., Cincinnati, Ohio

[73] Assignee: The Procter & Gamble Company, Cincinnati, Ohio

[21] Appl. No.: 09/049,329

[22] Filed: Mar. 27, 1998

Related U.S. Patent Documents

Reissue of:

[64] Patent No.: 5,626,838
Issued: May 6, 1997
Appl. No.: 08/402,587
Filed: Mar. 13, 1995

[51] Int. Cl.[6] ..... A61K 47/36

[52] U.S. Cl. ..... 424/54; 424/49; 424/55; 514/226.5; 514/255; 514/352; 514/365; 514/407; 514/411; 514/413; 514/427; 514/428; 514/448; 514/555; 514/900; 514/902

[58] Field of Search ..... 514/226.5, 255, 514/352, 365, 407, 411, 413, 427, 428, 448, 555, 900, 902; 424/54, 49, 55

[56] References Cited

U.S. PATENT DOCUMENTS

| | | | |
|---|---|---|---|
| 4,748,174 | 5/1988 | Veronesi | 514/226.5 |
| 5,464,609 | 11/1995 | Kelm et al. | 424/54 |

FOREIGN PATENT DOCUMENTS

| | | | |
|---|---|---|---|
| WO 91/10680 | 7/1991 | WIPO | C07K 13/00 |
| WO 91/13609 | 9/1991 | WIPO | A61K 7/22 |
| WO 93/16732 | 9/1993 | WIPO | A61K 47/36 |

OTHER PUBLICATIONS

Tanaka, T., et al., Cancer Letters, 48 (1989), pp. 177–182, "Inhibitory Effects of Non–Steroidal Anti–Inflammatory Drugs, Piroxicam and Indomethican on 4–nitroquinoline 1–Oxide–Induced Tongue Carcinogenesis in Male ACI/N Rats".

DeCosse, Jerome J., American Cancer Society, pp. 2550–2553, "Potential for Chemoprevention".

Hirsch, Barry, et al., Arch Otolaryngol—vol. 109, May 1983, pp. 298–301, "Immunostimulation of Patients with Head and Neck Cancer".

Pinto, S., et al., Prostaglandins Leukotrienes and Essential Fatty Acids (1990), pp. 53–57, "Prostaglandins in Squamous Cell Carcinoma of the Larynx: Tumor and Peritumor Synthesis".

Snyderman, Carl H., et al., Otolaryngology—Head and Neck Surgery (1994), pp. 184–196, "Comparison of in vivo and in vitro Prostaglandin $E_2$ Production By Squamous Cell Carcinoma of the Head and Neck".

Hancock, A. B., Cancer Research 52 (1992), pp. 5575–5589, "Aspirin and the Potential Role of Prostaglandins in Colon Cancer".

Regezi, Joseph, et al., Oral Pathology: Clinical–Pathologic Correlations, Second Edition, pp. 77–88, "Ulcerative Conditions" (1993.

Resman–Targoff, B. H., DICP, The Annals of Pharmacotherapy, vol. 24 (1990), pp. 1098–1104, "Ketorolac: A Parenteral Nonsteroidal Antiflammatory Drug".

Cameron, Deborah J., et al., Cancer vol. 54 (1984), pp. 2403–2408, "The Ability of Macrophages From Head and Neck Cancer Patients to Kill Tumor Cells".

Colacchio, Thomas A., et al., The American Journal of Surgery, vol. 167 (1994), pp. 174–179, "Perioperative Immunomodulation in Cancer Surgery".

Goodwin, James S., Journal of Immunopharmacology, 2(4) (1990), pp. 397–424, "Prostaglandin Synthetase Inhibitors as Immunoadjuvants in the Treatment of Cancer".

Earnest, David L., et al., Journal of Cellular Biochemistry, Supp. 161 (1992), pp. 156–166, "Piroxicam and Other Cyclooxygenase Inhibitors: Potential for Cancer Chemoprevention".

Panje, William R., Arch Otolaryngol, vol. 107 (1981), pp. 658–663, "Regression of Head and Neck Carcinoma with a Prostaglandin–Synthesis Inhibitor".

*Primary Examiner*—Frederick Krass
*Attorney, Agent, or Firm*—Loy M. White; Douglas C. Mohl; T. David Reed

[57] ABSTRACT

The present invention provides novel methods for prevention or treatment of primary and recurring squamous cell carcinoma of the oral cavity or oropharynx comprising topical administration, to the oral cavity or oropharynx, of an effective amount of an NSAID, especially a composition administering from about 0.001% to about 0.2% ketorolac to the oral cavity, alone or as an adjunct to surgery and/or radiation therapy.

16 Claims, No Drawings

USE OF KETOROLAC FOR TREATMENT OF SQUAMOUS CELL CARCINOMAS OF THE ORAL CAVITY OR OROPHARYNX

Matter enclosed in heavy brackets [ ] appears in the original patent but forms no part of this reissue specification; matter printed in italics indicates the additions made by reissue.

TECHNICAL FIELD

The present invention relates to methods for the prevention and treatment of primary and recurring squamous cell carcinomas of the oral cavity or oropharynx.

BACKGROUND OF THE INVENTION

It is generally accepted that one of the immune system's major roles is that of immunological surveillance to destroy abnormal cells. There has been extensive research to determine the defect in immune function that allows a tumor cell to escape this surveillance and subsequently develop into a viable tumor. It has been postulated that tumors develop because of general immune suppression. However, if general immune suppression occurs, only certain types of neoplastic disorders usually develop, such as those involving the lympho-reticular system. It has been suggested that prostaglandins play a significant role in the regulation of the local immune response, as well as carcinogen activation and tumor initiation. Therefore, more recent studies have focused on localized immune suppression. Experimental work has shown that, during the development of tumors, host macrophage are triggered to produce high levels of prostaglandin $E_2$ ($PGE_2$). Monocytes, lymphoid cells, and many tumor cells have also been shown to produce high levels of prostaglandins. The immunosuppressive effects of $PGE_2$ include the inhibition of: T and B lymphocyte proliferation, lymphokine production, cytotoxicity of natural killer (NK) cells, effector functions of T-cells, B-cells, and macrophages, and generation of cytotoxic T lymphocytes and lymphokine-activated killer (LAK) cells.

Studies using prostaglandin synthesis inhibitors, like nonsteroidal anti-inflammatory drugs (NSAID), have provided further evidence for the role of prostaglandins in mediating immunosuppression. Considerable evidence further suggests that NSAIDs may have an important role in chemoprevention. The use of NSAIDs, such as aspirin, indomethacin, piroxicam and fluorbiprofen, has been shown effective in reducing or inhibiting tumor growth and bone metastasis.

PCT Patent Publication WO93/16732 (Falk, et al.) teaches compositions, in the form of a gel or awn which are suitable for topical application comprising pharmaceutical excipients (1–5%, by weight) and an effective amount of hyaluronic acid (1–3%, by weight) sufficient to transport the drug to a site in the skin including epidermis, or exposed tissue of a disease or condition. The pharmaceutical excipients include nonsteroidal anti-inflammatory drugs selected from the group comprising diclofenac, indomethacia, naproxen, (+/−) tromethamine salt of ketorolac, ibuprofen, piroxicam propionic acid derivatives, acetylsalicylic acid, and fiunixin. Other pharmaceutical excipients include anticancer drugs selected from the group comprising Novantrone and 5-Fu (Fluorouracil). The compositions are claimed to be effective in the treatment of diseases and/or conditions selected from the group comprised of at least one basal cell carcinoma, actinic keratoses lesions, fungal lesions, "liver" spots, squamous cell tumors, metastatic cancer of the breast to the skin, primary and metastatic melanoma in the skin, genital warts, cervical cancer. Human Papilloma Virus of the cervix, psoriasis, corns of the feel and hair loss on the head of pregnant women.

Falk, et al, postulates that the use of an NSAID prevents the enzymatic production of prostaglandins, which block macrophage and Natural Killer (NK) cell functions in the local anti-tumor immune response. They suggest that the hyaluronic acid enhances the activity of prostaglandin synthesis inhibition and reduces any side effects that are associated with the use of the NSAID. Hyaluronic acid passes between the cells to the areas of trauma and/or pathology, transporting the NSAID with it, until the space between the cells is saturated. This allows the drug to remain at the areas of trauma and/or pathology for prolonged periods. The composition is subsequently cleared through tile lymphatic system.

Worldwide, oral carcinoma is one of the most prevalent cancers. Cancers of the oral cavity and oropharynx account for approximately 3% of all cancers diagnosed in the United States each year. Approximately 95% of all oral cancers occur in people older than 40 years of age and represents about 4% of total body cancers in males and about 2% in women. The survival rate is about 50% and deaths due to oral and oropharyngeal cancers represent approximately 2% of the total cancer related deaths in men and 1% in women, making it one of the 10 most common causes of death. The majority of oral cancers are squamous cell carcinomas and most commonly involve the tongue, oropharynx, and floor of the mouth, with the lips, gingiva, dorsal tongue, and palate being less common sites.

Surgery and/or radiation therapy are the current treatments of choice for oral cancers, such as squamous cell carcinoma. Chemotherapeutic agents, such as methotrexate, bleomycin, cisplatin, and 5-Fluorouracil, may reduce tumor bulk and delay metastasis, but the profound morbidity associated with this type of treatment may not justify their use as the only treatment modalities. Therefore, most current chemotherapeutic agents are used primarily as adjunctive therapy to surgery and/or radiation therapy in advanced cases of disease.

Patients with squamous cell carcinoma often have deficiencies in cellular and humoral immune functions. Immunosuppression observed in these patients is variable but appears to be the greatest at local and regional levels and several studies have demonstrated significant elevations of $PGE_2$ in tumor specimens from these patients.

It is an object of the present invention to provide a topical prevention and treatment of primary and/or recurring squamous cell carcinoma of the oral cavity and oropharynx using an NSAID, alone or as an adjunct to surgery and/or radiation therapy.

It is also an object of the present invention to provide a topical prevention and treatment of primary and/or recurring squamous cell carcinoma of the oral cavity and oropharynx using ketorolac, alone or as an adjunct to surgery and/or radiation therapy.

It is a further object of the present invention to provide such treatments which result in a minimal systemic (blood) concentration of ketorolac.

All percentages and ratios used herein are by weight, and all measurements made at 25° C., unless otherwise specified.

SUMMARY OF THE INVENTION

The present invention provides novel methods for prevention or treatment of primary and/or recurring squamous cell carcinomas of the oral cavity or oropharynx comprising topical administration, to tile oral cavity or oropharynx, of an effective amount of an NSAID, alone or as an adjunct to surgery and/or radiation therapy.

The present invention also provides novel methods and compositions for prevention or treatment of primary and/or recurring squamous cell carcinomas of the oral cavity or oropharynx comprising topical administration, to the oral cavity or oropharynx, of a composition providing from about 0.001% to about 0.2% by weight, of ketorolac to the oral cavity or oropharynx, alone or as an adjunct to surgery and/or radiation therapy.

DETAILED DESCRIPTION OF THE INVENTION

The preferred NSAID for purposes of these novel methods and compositions for the prevention and treatment of primary and/or recurring squamous cell carcinoma of the oral cavity or oropharynx is ketorolac, but others of comparable anti-inflammatory activity which are compatible with oral use are also useful. Such NSAIDs may include, but are not limited to, the following: aspirin, ibuprofen, naproxen, indomethacin, piroxicam, flurbiprofen, meclofenamate sodium ketoprofen, tenidap, tebufelone, and the like.

"Safe and effective amount", as used herein, means an amount of a substance high enough to provide a significant positive modification of the condition to be treated, but low enough to avoid serious side effects (at a reasonable benefit/risk ratio), within the scope of sound medical judgment. A safe and effective amount of the substance win vary with the particular condition being treated, the severity of the condition, the duration of the treatment, the nature of concurrent therapy, and like factors.

"Treat" and "treatment", as used herein, mean to attempt to slow the progress of or to reverse the symptoms of the condition being addressed.

"Effective" and "efficacy", as used herein, mean successful treatment resulting in slowing, halting, or reversing the adverse condition being addressed.

"Topical, oral carrier", as used herein, denotes a carrier for the NSAID which results in a composition which is administered topically to the oral cavity, held therein for a period of time, and then is largely expectorated rather than being swallowed. Such compositions include toothpastes, tooth gels, tooth powders, mouthwashes, mouthsprays, prophylaxis pastes, dental treatment solutions, and the like.

"Topical application", as used herein, means applied so as to contact exposed surfaces of the oral cavity with a composition or compound administered to the exposed surfaces of the oral cavity, preferably by swishing around in the mouth or brushing onto the teeth and/or over oral surfaces, or administered so as to inject or specifically insert into interior cavities, e.g., periodontal pockets, within the oral cavity. Application may also be accomplished by painting the composition or compound onto the oral cavity tissue afflicted with squamous cell carcinoma with a swab, gauze, sponge, or cotton ball. The composition or compound is then preferably largely expectorated except when injected or inserted into interior cavities or swabbed onto the oral cavity tissue afflicted with squamous cell carcinoma.

"Compatible" as used herein, means that the components of the compositions are capable of being co-mingled with one another, in a manner such that there is no interaction which would substantially reduce the efficacy of the oral composition under ordinary use conditions.

"Ketorolac", as used herein, is (±)5(benzoyl)-2,3-dihydro-1H-pyrrolizine-1carboxylic acid, and the pharmaceutically acceptable non-toxic esters and salts thereof, as disclosed in U.S. Pat. No. 4,089,969 issued to Muchowski & Kluge on May 16, 1978 which is incorporated by reference herein. The (−)-S enantiomer of ketorolac is preferred.

Pharmaceutically acceptable esters of ketorolac include but are not limited to, alkyl esters derived from hydrocarbons of branched or straight chain having one to about 12 carbon atoms. Examples of such esters are methyl, ethyl, propyl, isopropyl, butyl, t-butyl, isoamyl, pentyl, isopentyl, hexyl, octyl, nonyl, isodecyl, 6-methyldecyl and dodecyl esters.

Pharmaceutically acceptable salts of ketorolac include salts derived from either inorganic or organic bases. Salts derived from inorganic bases include sodium potassium, lithium ammonium, calcium, magnesium, ferrous, zinc, copper, manganese, aluminum, ferric, manganic salts and the like. Particularly preferred are the ammonium, potassium, sodium, and lithium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

The preferred ketorolac salt, which is soluble in the composition of the subject invention in which it is incorporated, for use in the compositions and methods of the present invention is the racemic mixture of (+)R and (−)-S enantiomer of ketorolac tromethamine, and most preferred is its (−)-S enantiomer, (−)-5(benzoyl)-2,3-dihydro-1H-pyrrolizine-1-carboxylic acid, 2-amino-2-(hydroxymethyl)-1,3-propanediol:

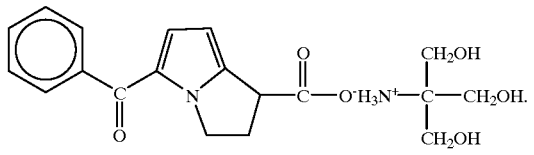

One aspect of the present invention is compositions comprising a safe and effective amount, preferably from about 0.001% to about 5%, more preferably from about 0.005% to about 1%, more preferably still from about 0.01% to about 0.5%, still more preferably from about 0.05% to about 0.2% ketorolac, and a pharmaceutically acceptable topical, oral carrier.

Also preferred are compositions comprising less than about 0.15% ketorolac, those comprising less than about 0.1% ketorolac and those comprising less than about 0.025% ketorolac.

Further preferred are compositions comprising less than about 0.1% hyaluronic acid, those comprising less than about 0.01% hyaluronic acid, and those comprising 0.00% hyaluronic acid.

When mouthwashes and dental solutions having the above concentrations of ketorolac are used in the oral cavity, the effective concentrations of ketorolac solutions which contact the oral cavity are essentially the same as given above, because dilution of the mouthwash or dental solution with saliva and water is minimal.

On the other hand, it is well known that dentifrices, when used in the mouth are mixed with substantial amounts of saliva and water the dilution amount is about 3:1 saliva to dentifrice (See U.S. Pat. No. 4,358,437, issued Nov. 9, 1982 to Duke, and U.S. Pat. No. 3,956,480 issued May 11, 1976 to Dichter et al.). Therefore, the effective concentration of NSAID solution in the mouth in contact with the oral cavity when a dentifrice is used, is about one-fourth the concentration of the NSAID in the dentifrice. Therefore, preferred concentrations of NSAID in a dentifrice are about four times the above preferred mouthwash concentrations: from about 0.004% to about 20% to administer from about 0.001% to about 5% of the NSAID. More preferable is a concentration of from about 0.02% to about 4%, more preferable still is from about 0.04% to about 2%, still more preferable is from about 0.2% to about 0.8% of the NSAID to administer from about 0.005% to about 1%, from about 0.01% to about 0.5%, and from about 0.05% to about 0.2% of the NSAID, respectively. Also preferred are dentifrice compositions comprising less than about 0.6% of the NSAID, those comprising less than about 0.4% of the NSAID, those comprising less than about 0.15%, and those comprising less than about 0.1% of the NSAID to administer less than about 0.15%, less than about 0.1%, less than about 0.0375% and less than about 0.025% of the NSAID, respectively.

The pH of the compositions of the present invention for which pH can be measured is preferably from about 2 to about 9, more preferably from about 4 to about 7, more preferably still from about 5 to about 6.

Components of the topical, oral carrier are suitable for administration to the oral cavity of a human or mammal and are compatible with one another and the other components, especially the NSAID, used in an oral composition of the present invention. Preferred topical, oral carriers thus provide the desired characteristics for toothpastes, tooth gels, tooth powders, mouthwashes, mouthsprays, prophylaxis pastes, dental treatment solutions, and the like. The topical, oral carriers of the present invention comprise components typically used in such compositions which are well known to a skilled practitioner. Such components include, but are not limited to anticaries agents, antiplaque agents, anticalculus agents, dental abrasives, surfactants, flavoring agents, sweetening agents, binders, humectants, thickening agents, buffering agents, preservatives, coloring agents and pigments, ethanol, and water.

Water is an optional component of the topical, oral carriers of the compositions of the present invention. Water employed in the preparation of the commercially suitable compositions should preferably be of low ion content and free of organic impurities. Water preferably comprises from about 2% to about 99%, more preferably from about 20% to about 95% of the compositions of the present invention. When in the form of toothpastes, the compositions preferably are from about 2% to about 45%, more preferably from about 30% to about 40%, water, while mouthwashes are preferably from about 45% to about 95%, more preferably from about 75% to about 90%, water.

Dental abrasives useful in the topical, oral carriers of the compositions of the present invention include many different materials. The material selected must be one which is compatible within the composition of interest and does not excessively abrade dentin. Suitable abrasives include, for example, silicas including gels and precipitates, insoluble sodium polymetaphosphate, hydrated alumina and resinous abrasive materials.

A class of preferred abrasives for use in the subject compositions is the particulate thermosetting polymerized resins as described in U.S. Pat. No. 3,070,510 issued to Cooley & Grabenstetter on Dec. 25, 1962. Suitable resins include, for example, melamines, phenolics, ureas, melamine ureas, metamine formaldehydes, urea formaldehydes, melamine urea formaldehydes, cross-linked epoxides, and cross-linked polyesters.

Silica dental abrasives are also preferred in the compositions of the present invention. The silica abrasive polishing material generally has an average particle size ranging between about 0.1 and about 30 microns, preferably between 5 and 15 microns. The abrasive can be precipitated silica or silica gels such as the silica xerogels described in U.S. Pat. No. 3,538,230 issued to Pader & Wiesner on Mar. 2, 1970, and in U.S. Pat. No. 3,862,307 issued to DiGuilio on Jan. 21, 1975. Preferred are the silica xerogels marketed under the tradename SyloidR, by the W. R. Grace & Co., Davison Chemical Division. Preferred precipitated silica materials are those marketed by the J.M. Huber Corporation under the tradename ZeodentR, particularly the silica carrying the designation Zeodent 119R. These silica abrasives are described in U.S. Pat. No. 4,340,583 issued to Wason on Jul. 29 , 1982.

Mixtures of abrasives can be used. All of the above patents regarding dental abrasives are incorporated herein by reference.

The total amount of abrasive in dentifrice compositions of the present invention preferably range from about 10% to about 70% by weight; toothpastes preferably contain from about 10% to about 50% by weight of abrasives. Solution, mouthspray and mouthwash compositions of the present invention may contain quantities of abrasive as low as 0%.

Flavoring agents are preferred in the topical, oral carriers of the compositions of the present invention in order to make them more palatable. Typical flavoring agents include menthol, oil of wintergreen, oil of peppermint, oil of spearmint, oil of sassafras, and oil of clove. If present, flavoring agents are generally included in the subject compositions in amounts of from about 0.04% to about 2% by weight.

Sweetening agents are also preferred in the topical, oral carriers of the compositions of the present invention in order to make them more palatable. Typical sweetening agents include saccharin salts, dextrose, levulose, thaumatin, aspartame, D-tryptophan, dihydrochalcones, acesulfame and cyclamate salts, especially sodium cyclamate and sodium saccharin. If present, sweetening agents are generally included in the subject compositions in amounts of from about 0.01% to about 5% by weight.

Another optional component of the topical, oral carriers of the compositions of the present invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 2% to about 55%, by weight of the compositions herein. Suitable humectants for use in compositions of the present invention include edible polyhydric alcohols such as glycerin, sorbitol, xylitol, polyethylene glycol, and propylene glycol, especially sorbitol and glycerin.

Buffering agents are another optional component of the topical, oral carrier of the compositions of the present Invention. The buffering agents serve to retain the pH of the compositions within the preferred range. The buffering agent generally comprises from about, 0% to about 10%, preferably from about 0.2% to about 5%, by weight of the compositions herein. Suitable buffering agents for use in compositions of the present invention include soluble phosphate salts.

Other optional components of the topical, oral carriers of the compositions of the present invention are preservatives. The preservatives prevent microbial growth in the compositions. Suitable preservatives include methylparaben, propylparaben, benzoates and ethanol. If the preservative is ethanol, it generally comprises from 0% to bout 35%, preferably from about 5% to about 15%, of the compositions herein. Other preservatives generally comprise from about 0% to about 5%, preferably from about 0.1% to about 2%, by weight of the compositions herein.

Binders and thickening agents may be used in the topical, oral carriers of the compositions of the present invention particularly in toothpaste compositions. Preferred binders and thickening agents include, for example, carrageenan (e.g.. Irish moss. Viscarin TP-5 which is an iota carrageenan), cellulose derivatives (e.g., hydroxyethyl cellulose, sodium carboxymethyl cellulose, sodium carboxymethyl hydroxypropyl cellulose), carboxyvinyl polymers (carbomers), natural gums (e.g., gum karaya, gum arabic, gum tragacanth), polysaccharide gums (e.g., xanthan gum), fumed silica and colloidal magnesium aluminum silicate. If present, these binders and thickening agents are generally present in the compositions of the present invention in amounts of from about 0.1% to about 5%.

Compositions of the present invention may also contain a surfactant. Suitable surfactants are those which are reasonably stable and preferably form suds through the pH range of the compositions. Surfactants useful as sudsing agents may be soaps, and anionic, nonionic, cationic, zwitterionic and amphoteric organic synthetic detergents, and compatible mixtures thereof. Surfactants of these types are described more fully in U.S. Pat. No. 3,959,458 issued to Agricola, Briner, Granger & Widder on May 25, 1976, incorporated herein by reference. Such surfactants are generally present in the compositions of the present invention at a level of from about 0%, to about 10%, preferably from about 0.2% to about 5%. Surfactants may also be used as solubilizing agents to help retain sparingly soluble components, e.g., some flavoring agents, in solutions. Surfactants suitable for this purpose include polysorbates and poloxamers.

The compositions of the present invention may also comprise an anticaries agent. Preferred anticaries agents are water-soluble fluoride ion sources. The number of such fluoride ion sources is great and includes those disclosed in U.S. Pat. No. 3,535,421 issued Oct. 20, 1970 to Briner & Widder, incorporated herein by reference. Preferred fluoride ion source materials include: sodium fluoride, potassium fluoride, and sodium monofluorophosphate and mixtures thereof. Sodium fluoride is the preferred fluoride source. The amount of the fluoride ion source in the oral compositions of the present invention, if present, is preferably sufficient to provide from about 0.005% to about 0.35%, more preferably from about 0.05% to about 0.3% of fluoride ions in the compositions.

Antimicrobial antiplaque agents can also optionally be present in the oral compositions of the present invention, on the condition that they are compatible with the NSAID. Such agents may include Triclosan, 5-chloro-2-(2,4-dichlorophenoxy)-phenol, as described in The Merck Index, 10th ed. (1976), p. 1381; U.S. Pat. No. 3,506,720; and European Patent Application No. 0,251,591 of Beecham Group, PLC, published Jan. 7, 1988, chlorhexidine, (Merck Index, No. 2090), alexidine (Merck Index, No. 222); hexetidine (Merck Index, No. 4624); sanguinarine (Merck Index, No. 8320); benlkonium chloride (Merck Index, No. 1066); aalicylmide (Merck Index, No. 8299); domiphen bromide (Merck Index, No. 3411); cetylpyridinium chloride, (CPC) (Merck Index, No. 2024); tetradecylpyridinium chloride, (TPC): N-tetra-decyl-4-ethylpyridinium chloride (TDEPC); octenidine; delmopinol, octapinol, and other piperidino derivatives; nicin preparaons; zinctstannous ion agents; antibiotics such as augmentin, amoxicilin, tetracycline, doxycycline, minocycline, and metronidazole; and peroxides, such as cylium peroxide, hydrogen peroxide, and magnesium monoperthalate and its analogs as described in U.S. Pat. No. 4,670,252; and analogs and salts of the above antimicrobial antiplaque agents. If present, the antimicrobial antiplaque agents generally comprise from about 0.1% to about 5% by weight of the compositions of the present invention.

Nutrients can also be present in oral compositions of the present invention, on condition that they are compatible with the NSAID active. Such agents may include folate, retinoids (Vitamin A), Vitamin C, Vitamin E and zinc. If present, the nutrients generally comprise from about 0.001% to about 10% by weight of the compositions of the present invention.

Compositions of the present invention may also include one or more anticalculus agents, on the condition that they are compatible with the NSAID. Anticalculus agents which may be useful in the compositions of the present invention include pyrophosphates or polyphosphates such as those disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989: ethylenediaminetetmaaoetic acid as disclosed in British Patent No. 490384 dated Feb. 15, 1937; nitriotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt, Dunker & Gloxhuber on Oct. 26, 1976 and U.S. Pat. No. 4,877,603 issued to Degenhardt & Kozikowski on Oct. 31, 1989; all of these patents are incorporated herein by reference. If present, the anticalculus agents generally comprise from about 0.2% to about 13%, preferably from about 0.4% to about 6% of the compositions of the present invention.

Preferred compositions of the present invention are mouthwashes, mouthsprays, dental solutions, and toothpastes. Components of such mouthwashes and mouthsprays include water (from about 45% to about 95%), ethanol (from about 0% to about 25%), a humectant (from about 0% to about 50%), a surfactant agent (from about 0.01% to about 7%), an flavoring agent (from about 0.04% to about 2%), a sweetening agent (from about 0.1% to about 3%), and a coloring agent (from about 0.001% to about 0.5%). Such mouthwashes and mouthsprays may also include one or more of an anticaries agent (from about 0.05% to about 0.3% as fluoride ion), an anticalculus agent (from about 0.1% to about 3%), and an antiplaque agent (from about 0.1% to about 5%). Components of such dental solutions generally include water (from about 90% to about 99%), preservative (from about 0.01% to about 0.5%, thickening agent (from about 0% to about 5%), flavoring agent (from about 0.04% to about 2%), sweetening agent (from about 0.1% to about 3%), and surfactant (from 0% to about 5%). Components of such toothpastes generally include a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anticalculus agent (from about 0.1% to about 13%), and an antiplaque agent (from about 0.1% to about 5%).

The subject invention relates to a method for prevention or treatment of primary and/or recurring squamous cell carcinoma of the oral cavity or oropharynx comprising topical administration to the oral cavity of a composition having a safe and effective amount of NSAID, especially ketorolac, in the oral cavity, alone or as an adjunct to surgery and/or radiation therapy. Such compositions in the oral cavity preferably comprise from about 0.001% to about 5%. more preferably from about 0.001% to about 1%, more preferably from about 0.001% to about 0.2%, more preferably from about 0.01% to about 0.15%, also preferably from about 0.05% to about 0.1%, also preferably less than 0.025% ketorolac.

It has been found that the plasma concentration of ketorolac resulting from the methods of the present invention is very low. For example, the relative dose corrected bioavailability of ketorolac using 0.01–0.1% rinse formulations is 13–15%, compared to a 10 milligram ketorolac capsule.

In contrast to the low systemic concentrations of ketorolac which result from the topical administration methods of the present invention, peroral dosage of NSAIDs has been reported to result in high systemic concentration of the dosed NSAID. This unexpected benefit resulting from topical application of ketorolac compositions is highly desirable, because it avoids the adverse side effects of high systemic concentration of NSAIDs and allows for continuous chronic administration of the drug. It is well known that possible adverse effects from the peroral use and/or high systemic concentrations of NSAIDs include nausea indigestion, diarrhea and peptic ulcer, as well as more severe toxic side effects (see, The American Medical Association Encyclopedia of Medicine, 730 (C. Klayman. Ed., 1989); see also, D. R. Robinson, Osteoarhritis. Medicine 15:X (Scientific American, September 1991 )).

The methods of the present invention preferably involve the contact of a composition of the present invention with oral cavity tissue afflicted with squamous cell carcinoma for at least about 15 seconds, preferably from about 20 seconds to about 10 minutes, more preferably from about 30 seconds to about 60 seconds. Typically, this is achieved by conventional methods of tooth brushing, rinsing the mouth with mouthwash or dental solution, etc. The composition is placed in the mouth, swished around or brushed on the teeth and oral surfaces and largely expectorant. The composition of the present invention may also be administered so as to inject or specifically insert into interior cavities, e.g., periodontal pockets, within the oral cavity. Application may also be accomplished by painting the composition onto the oral cavity tissue afflicted with squamous cell carcinoma with a swab, gauze, sponge, or cotton ball.

The following examples are provided as illustrations of the composition and methods of the present invention, but are not limitations of the scope of the present invention.

EXAMPLES 1 AND 2

Examples of toothpaste compositions of the present invention are as follows:

| Ingredients | Example 1 (Wt. %) | Example 2 (Wt. %) |
|---|---|---|
| Sorbitol | 42.00 | 35.00 |
| Saccharin Sodium | 0.13 | 0.20 |
| FD&C Blue (1% soln) | 0.05 | 0.05 |
| Precipitated Silica | 20.00 | 25.00 |
| Sodium Fluoride | 0.00 | 0.24 |
| Flavor | 0.90 | 1.50 |
| Purified Water | qs | qs |
| Sodium Alkyl Sulfate | 1.00 | 1.20 |
| Phosphoric Acid | 0.40 | 0.00 |
| Carbomer 94 | 0.25 | 0.25 |
| Xanthan Gum | 0.50 | 0.65 |
| Titanium Dioxide | 0.50 | 0.50 |
| Ketcrolac Tromethamine | 0.05 | 0.10 |

EXAMPLES 3, 4 AND 5

Examples of mouthwash compositions of the present invention are as follows:

| Ingredients | Example 3 (Wt. %) | Example 4 (Wt. %) | Example 5 (Wt. %) |
|---|---|---|---|
| Ketorolac Tromethamine | 0.10 | 0.01 | 0.10 |
| Ethanol | 12.00 | 15.00 | 0.00 |
| Glycerin | 10.00 | 12.00 | 12.00 |
| Propylene Glycol | 0.00 | 0.00 | 10.00 |
| Dibasic Sodium Phosphate, Heptahydrate | 0.07 | 0.48 | 0.00 |
| Saccharin Sodium | 0.08 | 0.08 | 0.06 |
| Monobasic Sodium Phosphage, Monohydrate | 2.03 | 1.82 | 0.00 |
| Polyethylene Glycol 40 | 0.00 | 0.00 | 0.30 |
| Sodium Benzoate | 0.00 | 0.00 | 0.42 |
| Benzoic Acid | 0.00 | 0.00 | 0.075 |
| Polysorbate 80 | 0.33 | 0.33 | 0.10 |
| FD&C Blue (1% Soln) | 0.02 | 0.02 | 0.00 |
| Color Solution | 0.00 | 0.00 | 0.02 |
| Flavor | 0.15 | 0.15 | 0.10 |
| Purified Water | qs | qs | qs |

*Color Solution (1%) is made with 0.46% FD&C yellow #5 and 0.54% FD&C blue #1.

EXAMPLE 6

An example of a dental solution of the present invention is as follows:

| Ingredients | Example 6 (Wt. %) |
|---|---|
| Water | qs |
| Ketorolac Tromethamine | 0.15 |
| Flavor | 0.10 |
| Polysorbate 80 | 0.25 |
| Saccharin Sodium | 0.05 |
| Methylparaben | 0.20 |
| Propylparaben | 0.10 |

EXAMPLES 7 AND 8

Examples of toothpaste compositions of the present invention are as follows:

| Ingredients | Example 7 (Wt. %) | Example 8 (Wt. %) |
|---|---|---|
| Sorbitol | 37.20 | 37.20 |
| Glycerin | 19.00 | 19.00 |
| Polyethylene Glycol 600 | 3.00 | 3.00 |
| Sodium Saccharin | 0.17 | 0.17 |
| Precipitated Silica | 20.00 | 20.00 |
| Sodium Fluoride | 0.24 | 0.24 |
| Flavor | 0.90 | 0.90 |
| Purified Water | qs | qs |
| Sodium Alkyl Sulfite | 1.00 | 1.00 |
| Monbasic Sodium Phosphate, Monohydrate | 5.00 | 5.00 |
| Fumed Silica | 2.00 | 2.00 |
| Carboxymethylcellulose | 0.30 | 0.30 |
| Titanium Dioxioe | 0.50 | 0.50 |
| Ketorolac Tromethamine | 0.15 | 1.00 |

While particular embodiments of the present invention have been described, it will be obvious to those skilled in the art that various changes and modifications to the present invention can be made without departing from the spirit and scope of the invention. In the foregoing examples, other NSAIDs herein described such as aspirin, ibuprofen, naproxen, indomethacin, piroxidcam, flurbiprofen, meclofenamate sodium ketoprofen, tenidap, tebufelone, and the like, may replace ketorolac tromethamine, in concentrations providing a safe and effective amount of the drug to the oral cavity or oropharynx. Likewise other components within the groups of this invention such as anticaries agents, antiplaque agents, anticalculus agents, dental abrasives, surfactants, flavoring agents, sweetening agents, binders, humectants, thickening agents, buffering agents, preservatives, coloring agents and pigments, ethanol, and water, as described herein, may replace the groups component specifically listed in the foregoing examples. It is intended to cover, in the appended claims, all such modifications that are within the scope of this invention.

What is claimed is:

1. A method of treatment for primary and recurring squamous cell carcinoma of the oral cavity or oropharynx of a human or mammal having said carcinoma comprising the topical administration to the oral cavity or oropharynx of said human or lower animal, of a composition, free of hyaluronic acid, comprising an effective amount of an NSAID, alone or as an adjunct to surgery and/or radiation therapy, wherein said composition is held in the oral cavity for a period of from about 15 seconds to about 10 minutes, then largely expectorated rather than being swallowed.

2. A method according to claim 1 wherein the NSAID is selected from the group consisting of aspirin, ibuprofen, naproxen, indomethacin, piroxicam flurbiprofen, meclofenamate sodium, ketoprofen, tenidap, tebufelone, ketorolac, and mixtures thereof.

3. A method according to claim 1 wherein the NSAID is ketorolac.

4. A method of treatment for primary and recurring squamous cell carcinoma of the oral cavity or oropharynx of a human or mammal having said carcinoma comprising the topical administration to the oral cavity or oropharynx of said human or lower animal, of a composition, free of hyaluronic acid, providing from about 0.001% to about 0.2%, by weight of ketorolac to the oral cavity or oropharynx, alone or as an adjunct to surgery and/or radiation therapy, wherein said composition is held in the oral cavity for a period of from about 15 seconds to about 10 minutes, then largely expectorated rather than being swallowed.

5. A method according to claim 4 comprising topical administration of a composition providing from about 0.01% to about 0.15%, by weight of ketorolac to the oral cavity or oropharynx.

6. A method according to claim 5 wherein the ketorolac is ketorolac tromethamine.

7. A method according to claim 6 wherein the ketorolac tromethamine essentially consists of the (–)-S enantiomer.

8. A method according to claim 7 wherein said composition is in the form of a mouthwash, mouthspray, dental solution, or toothpaste.

*9. A method for the prophylaxis of primary and recurring squamous cell carcinoma of the oral cavity or oral pharynx of a human or mammal in need thereof, comprising the topical administration to the oral cavity or oropharynx of said human or mammal, of a composition free from hyaluronic acid, comprising an effective amount of an NSAID, alone or as an adjunct to surgery and/or radiation therapy, wherein said composition is held in the oral cavity for a period of from 15 seconds to about 10 minutes, then largely expectorated rather than being swallowed.*

*10. A method according to claim 9 wherein the NSAID is selected from the group consisting of aspirin, ibuprofen, naproxen, indomethacin, piroxicam, flurbiprofen, meclofenamate sodium, ketoprofen, tenidap, tebufelone, ketorolac, and mixtures thereof.*

*11. A method according to claim 10 wherein the NSAID is ketorolac.*

*12. A method for the prophylaxis of primary and recurring squamous cell carcinoma of the oral cavity or oral pharynx of a human or mammal in need thereof comprising the topical administration to the oral cavity or oropharynx of said human or mammal, of a composition free from hyaluronic acid, providing from about 0.001% to about 0.2% by weight of ketorolac, alone or as an adjunct to surgery and/or radiation therapy, wherein said composition is held in the oral cavity for a period of from 15 seconds to about 10 minutes, then largely expectorated rather than being swallowed.*

*13. A method according to claim 12 comprising topical administration of a composition providing from about 0.01% to about 0.15%, by weight of ketorolac to the oral cavity or oropharynx.*

*14. A method according to claim 13 wherein the ketorolac is ketorolac tromethamine.*

*15. A method according to claim 14 wherein the ketorolac tromethamine essentially consists of the (–)-S enantiomer.*

*16. A method according to claim 15 wherein said composition is in the form of a mouthwash, mouthspray, dental solution, or toothpaste.*

* * * * *